United States Patent
Williamson

(10) Patent No.: US 9,257,027 B2
(45) Date of Patent: Feb. 9, 2016

(54) DUCT DETECTOR

(75) Inventor: Alasdair James Williamson, Worthing (GB)

(73) Assignee: Xtralis Technologies, Ltd., Nassau (BS)

( * ) Notice: Subject to any disclaimer, the term of this patent is extended or adjusted under 35 U.S.C. 154(b) by 175 days.

(21) Appl. No.: 13/821,737

(22) PCT Filed: Sep. 9, 2011

(86) PCT No.: PCT/GB2011/051692
§ 371 (c)(1),
(2), (4) Date: Mar. 8, 2013

(87) PCT Pub. No.: WO2012/032359
PCT Pub. Date: Mar. 15, 2012

(65) Prior Publication Data
US 2013/0160571 A1 Jun. 27, 2013

(30) Foreign Application Priority Data
Sep. 10, 2010 (AU) ................. 2010904079

(51) Int. Cl.
*G01N 1/22* (2006.01)
*G01N 1/26* (2006.01)
*G08B 17/117* (2006.01)
*G08B 17/10* (2006.01)
*F16L 55/00* (2006.01)

(52) U.S. Cl.
CPC .............. *G08B 17/10* (2013.01); *F16L 55/00* (2013.01); *G01N 1/2247* (2013.01); *G01N 1/26* (2013.01); *G08B 17/117* (2013.01)

(58) Field of Classification Search
CPC .............. G01N 1/2247; G01N 1/26; G01N 2001/2285; G08B 17/117; G08B 17/10; F16L 55/00
USPC ........... 73/31.05, 863.41, 863.51, 863.53, 73/863.56
See application file for complete search history.

(56) References Cited

U.S. PATENT DOCUMENTS

| 2,834,208 | A |   | 6/1958 | Westman |
|---|---|---|---|---|
| 2,971,375 | A |   | 2/1961 | Fieldgate |
| 3,595,087 | A | * | 7/1971 | Starks ............... 73/863.54 |
| 3,803,921 | A | * | 4/1974 | Dieterich ............ 73/203 |

(Continued)

FOREIGN PATENT DOCUMENTS

| AU | 2006201261 A1 | 4/2006 |
|---|---|---|
| CN | 101762708 A | 6/2010 |
| DE | 196 05 637 C1 | 5/1997 |

OTHER PUBLICATIONS

International Search Report for PCT/GB2011/051692, Dated Mar. 16, 2012.

(Continued)

*Primary Examiner* — Daniel S Larkin
(74) *Attorney, Agent, or Firm* — Boyle Fredrickson, S.C.

(57) ABSTRACT

There is described a duct detector and components for duct detectors. In one form the duct detector includes: a port unit and detector unit. The port unit is mountable to a duct in use so as to position one or more ports in the duct. The detector unit includes a detection region. The port unit and detector unit are reconfigurable between a close coupled configuration and a separated configuration in which the units are mountable with a variable separation between them and coupled by one or more elongate conduits to provide fluid communication between the units.

11 Claims, 7 Drawing Sheets

(56) References Cited

U.S. PATENT DOCUMENTS

| | | | |
|---|---|---|---|
| 5,174,325 A * | 12/1992 | Okel et al. | 137/317 |
| 5,507,192 A | 4/1996 | Beaudin | |
| 5,756,908 A * | 5/1998 | Knollmeyer et al. | 73/866.5 |
| 5,834,657 A * | 11/1998 | Clawson et al. | 73/863.81 |
| 5,844,148 A * | 12/1998 | Klein et al. | 73/863.82 |
| 5,861,053 A * | 1/1999 | Noritake et al. | 96/111 |
| 6,282,943 B1 * | 9/2001 | Sanders et al. | 73/23.2 |
| 6,354,135 B1 * | 3/2002 | McGee et al. | 73/23.34 |
| 7,089,811 B2 * | 8/2006 | Allmendinger | 73/863.51 |
| 2001/0039824 A1 | 11/2001 | Sunshine et al. | |
| 2007/0084286 A1 | 4/2007 | Ajay et al. | |
| 2008/0001768 A1 | 1/2008 | Cole | |
| 2010/0194575 A1 | 8/2010 | Rodriguez | |

OTHER PUBLICATIONS

Johnson Controls; CD-Pxx-00-1 Series Duct Mount CO2 Transmitter Product Bulletin; Code No. LIT-216525; Issued Dec. 6, 2010; pp. 1-5.

* cited by examiner

DUCT DETECTOR

FIELD OF THE INVENTION

The invention relates to duct detectors and components for duct detectors.

BACKGROUND OF THE INVENTION

Duct detectors are a form of a detector mountable to a duct to provide an indication of a characteristic of the fluid flowing in the duct. For example, a duct detector in the form of a smoke detector can be mounted to a heating ventilation air-conditioning (HVAC) duct to detect smoke therein. Such an arrangement can provide an early indication of smoke in the HVAC system thereby enabling the HVAC system to be shut down to prevent smoke from one portion of the building being distributed about the building by the HVAC system.

HVAC ducts are often mounted within difficult working environments in roof spaces and the like. As such, installing duct detectors can be difficult, and the installation of the detector is sometimes compromised due to these difficult working conditions. For example, structure defining an HVAC plenum for dividing and directing flow from a single duct into four separate ducts might be inaccessible, thereby necessitating the installation of four separate detectors on the downstream ducts.

Moreover, duct detectors require maintenance from time to time, meaning that periodically maintenance personnel must return to these difficult working conditions.

UK patent application GB 2347541 describes a duct detector including an inlet and an outlet, which each open into the duct, and an aspirator in the form of a centrifugal blower to draw air from the duct via the inlet and direct the air toward a sensor before it returns to the duct via the outlet. Other duct detectors omit an aspirator and instead rely upon pressure differences between the inlet and the outlet so that flow in the duct drives fluid through the duct detector.

It is an object of the invention to provide an improved duct detector and components therefor, or at least to provide an alternative for those concerned with duct detectors.

It is not admitted that any of the information in this specification is common general knowledge, or that the person skilled in the art could reasonably be expected to have ascertained, understood, regarded it as relevant or combined it in anyway at the priority date.

SUMMARY OF THE INVENTION

Accordingly in its various aspects the invention provides duct detectors, various components therefor and methods of detection.

In a first aspect of the present invention there is provided a port unit for a duct detector, the unit including a portion mountable to a duct with one or more ports configured to open into the interior of the duct in use; and being: a unit separable from a portion of the duct detector including a detection region, and attachable to the portion of the duct detector including the detection region via one or more conduits to provide fluid communication between them.

The port unit is preferably a probe arrangement including a probe or probes having the one or more ports and extending from the mountable portion to extend into the interior of the duct to position the port(s) in the duct.

The probe can include: a portion having one or more ports and extending from the mountable portion to extend into the interior of the duct to position the port(s) in the duct; and structure to which an extension piece having one or more ports is mountable.

The unit can include mating structure configured to engage the portion of the duct detector including the detection region, to enable engagement of the port unit and portion of the duct detector including the detection region in a close coupled configuration. The mating structure could be configured to engage the one or more conduits to enable connection of the probe unit to the portion of the duct detector including the detection region when separated and mounted remotely from each other.

In a second aspect of the present invention there is provided a port unit for a duct detector, the port unit including: a portion mountable to a duct in use, a single probe for insertion into the duct in use and projecting from the mountable portion, the probe including a first passage having at least one inlet port for receiving a sample of flow from the duct; and a second passage having at least one outlet port for returning the sample to the duct; and a first fluid coupling being adapted for connection to an inlet of a particle detector and being in fluid communication with the first passage; and a second fluid coupling being adapted for connection to an outlet of a particle detector and being in fluid communication with the second passage. The probe could be rotatable relative to the portion mountable to the duct to enable the probe to be re-oriented with respect to the portion mountable to the duct, such that the at least one inlet and outlet are aligned with a direction of flow in the duct. The mountable portion and the probe preferably cooperate to define two separate manifold spaces, a first manifold space being in fluid communication with the first passage and first fluid coupling; and the second manifold space in fluid communication with the second passage and second fluid coupling.

In the above examples a probe can preferably include an indicator of the orientation of the probe(s) visible from outside the duct.

In another aspect of the present invention there is provided a duct detector including: a port unit including one or more ports, said port unit being mountable to a duct in use so as to position the one or more ports in the duct; and a detector unit including a detection region; said the port unit and detector unit being reconfigurable between a close coupled configuration and a separated configuration in which the units are mountable with a variable separation between them and coupled by one or more conduits to provide fluid communication therebetween.

The units can include cooperable mating structure by which the units are coupled when in the close coupled configuration.

The ports can include: one or more inlets for receiving a sample of flow from a duct; one or more outlets for returning the sample to the duct; and wherein the detection region is between the inlets and the outlets; the inlets and the outlets being configured such that in use, flow in the duct to which the port unit is mounted drives a sample flow through the detector for aspiratorless operation in the close coupled configuration.

The duct detector can further include structure for receiving an aspirator configured to drive a sample flow through the detector for aspirated operation. Preferably the detector includes an aspirator in the separated configuration.

Preferably in the close coupled configuration the port unit and detector unit are rigidly coupled to each other.

The port unit is preferably of a type described herein. Most preferably it is a port unit made in accordance with either of the first or second embodiments of the present invention. It could also include s probe arrangement according to one of the following aspects of the present invention.

The units may include cooperable mating structure by which the units are coupled when in the close coupled configuration. The port unit preferably includes a housing, and the detector unit preferably includes a housing. In this case in the close coupled configuration the housing of the port unit and detector unit are engaged with each other. Engagement can be direct, or via an intermediate member, such as a gasket or the like, or via connector that holds the housings in a fixed relationship with each other. The connector could be separable or removable to allow the units to be separated. The connector could include one or more short pipes connecting the ports of each unit to a corresponding port the other unit. The connectors are preferably received internally within the ports and provide mechanical engagement between the units and prevent leakage from the ports, when connected in the close coupled configuration.

In another fourth aspect of the present invention there is provided a probe arrangement for a duct detector. The arrangement preferably including: a portion mountable to a duct; and a probe or probes, having one or more ports and extending from the mountable portion to extend into the interior of the duct to position the port(s) in the duct; the probe or probes being reorientable relative to the mountable portion in use, to reorient the port(s) relative to flow in the duct independent of an orientation at which the portion mountable to the duct.

The ports can include one or more inlets, for receiving a sample of the flow, and one or more outlets for returning the sample to duct. The mountable portion can define, an intake passage portion, for conveying the sample from the inlets toward a detection region of the detector, and an exhaust passage portion for conveying the sample from the detection region to the outlets; each passage portion being fixed relative to the structure defining the duct.

Preferably the reorientation includes rotating the probe about an axis.

The mountable portion and the probe can be configured to cooperate to define two separate manifold spaces spaced in the direction of the axis; and the probe configured to have further ports for communicating the inlets with one of the manifold spaces and communicating the outlets with the other of the manifold spaces; each passage portion opening into a respective one of the manifold spaces. The inlet(s) and the outlet(s) preferably open in generally opposite directions.

The arrangement preferably includes a portion manipulable from outside the duct to so reorient the probe relative to the mountable portion. The arrangement can include an indicator of the orientation of the probe(s) visible from outside the duct.

The probe may include structure to which an extension piece having one or more ports is mountable.

In a fifth aspect of the present invention there is provided a duct detector including a probe arrangement of as described herein, preferably being made in accordance with the previous aspect of the present invention; and a detector housing including at least one detection region.

In a sixth aspect the present invention provides a duct detector including: one or more inlets for receiving a sample of flow from a duct; one or more outlets for returning the sample to the duct; a detection region between the inlet and the outlet; the inlets and the outlets being configurable for flow in the duct to drive the sample flow through the detector for aspiratorless operation; and structure for receiving an aspirator for aspirated operation.

In a seventh aspect the present invention provides a duct detector including: at least one inlet port for receiving an air sample from a duct; at least one detection region; at least one exhaust port for expelling the air sample; structure defining a flow path between said at least one inlet port and said at least one exhaust port via a detection region, said structure defining the flow path including mounting structure configured to carry an aspirator in the flow path for enabling aspirated operation of the duct detector; and also configured to maintain integrity of the flow path when not carrying an aspirator to enable aspiratorless operation of the detector.

The duct detector can further include an, or the, aspirator for motivating flow between the port(s) and the detection region.

The detector can include a flow detector in fluid communication with the port(s) to detect a flow through the detector.

Some embodiments can includes a plurality of detection regions. The, or each, detection region can include a detector configured to detect any one or more of: particles, smoke, gas. At least one detection region preferably comprises a chamber in which an air sample is analysed for the presence or level of a target species.

The duct detector can include at least one detector module is mounted in the chamber.

In another aspect the present invention provides a duct detector including: one or more inlets for receiving a sample of flow from a duct; a detector module for analysing the sample; a device for extracting power from the flow in the duct to generate electricity to power at least part of the duct detector.

The duct detector preferably includes an energy storage device to power at least part of the duct detector or the at least part of the duct detector, which storage device is preferably charged by the extraction device. The storage device may be or include one or more of a battery, and capacitor and a supercapacitor.

Optionally the extraction device includes one or both of an impeller and an oscillating flap. The extraction device is preferably directly exposed to the flow in the duct.

It will be appreciated that the various components could be sold together in various combinations; e.g. as installation, upgrade or maintenance kits. Such kits are within the ambit of the invention.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS/FIGURES

Illustrative embodiments of the present invention will be described by way of non-limiting example only with reference to the following figures. The Figures illustrate:

DETAILED DESCRIPTION OF THE EMBODIMENTS

Figure 1:
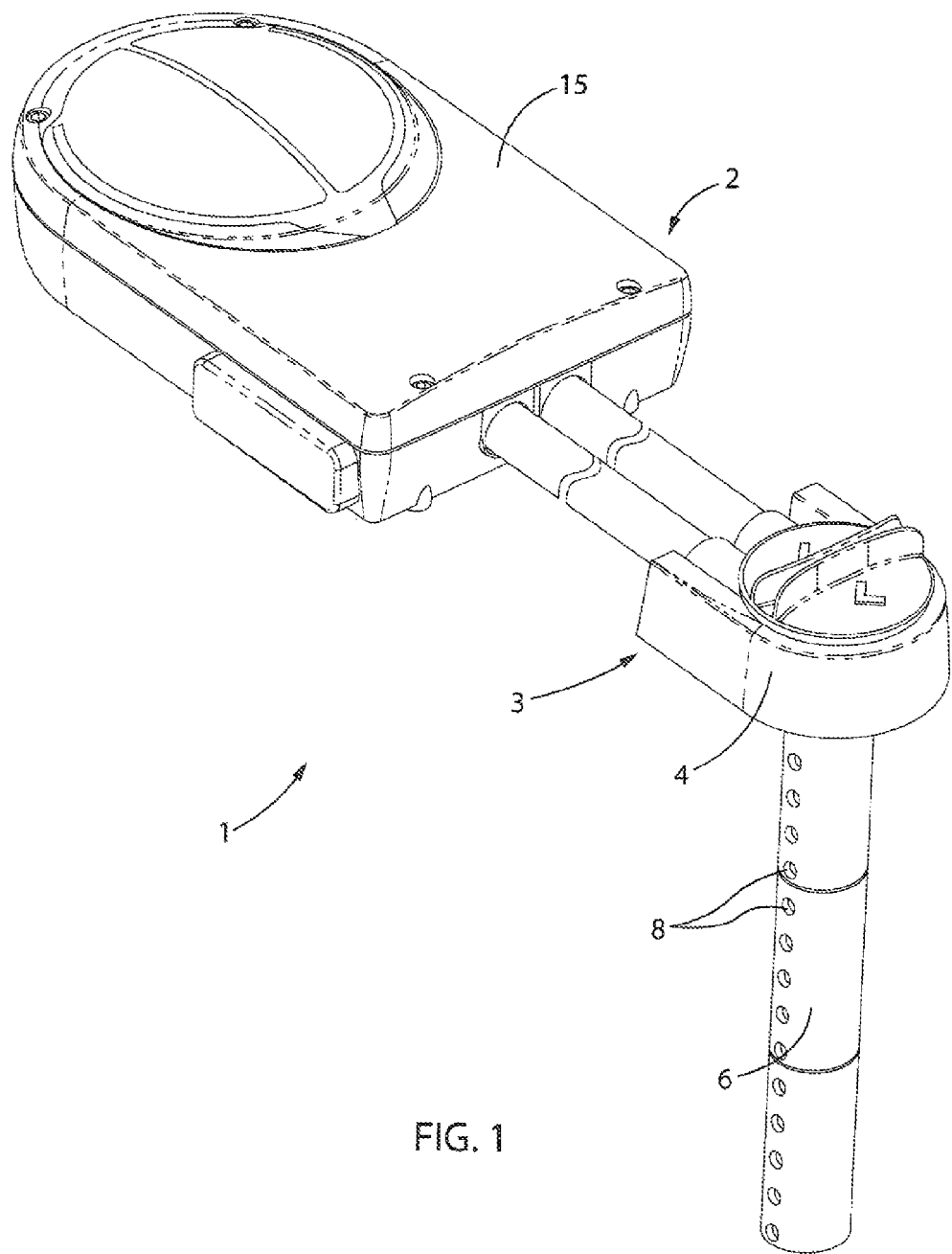
FIG. 1 is a perspective view of a duct detector in accordance with an embodiment of the invention.
Figure 2:
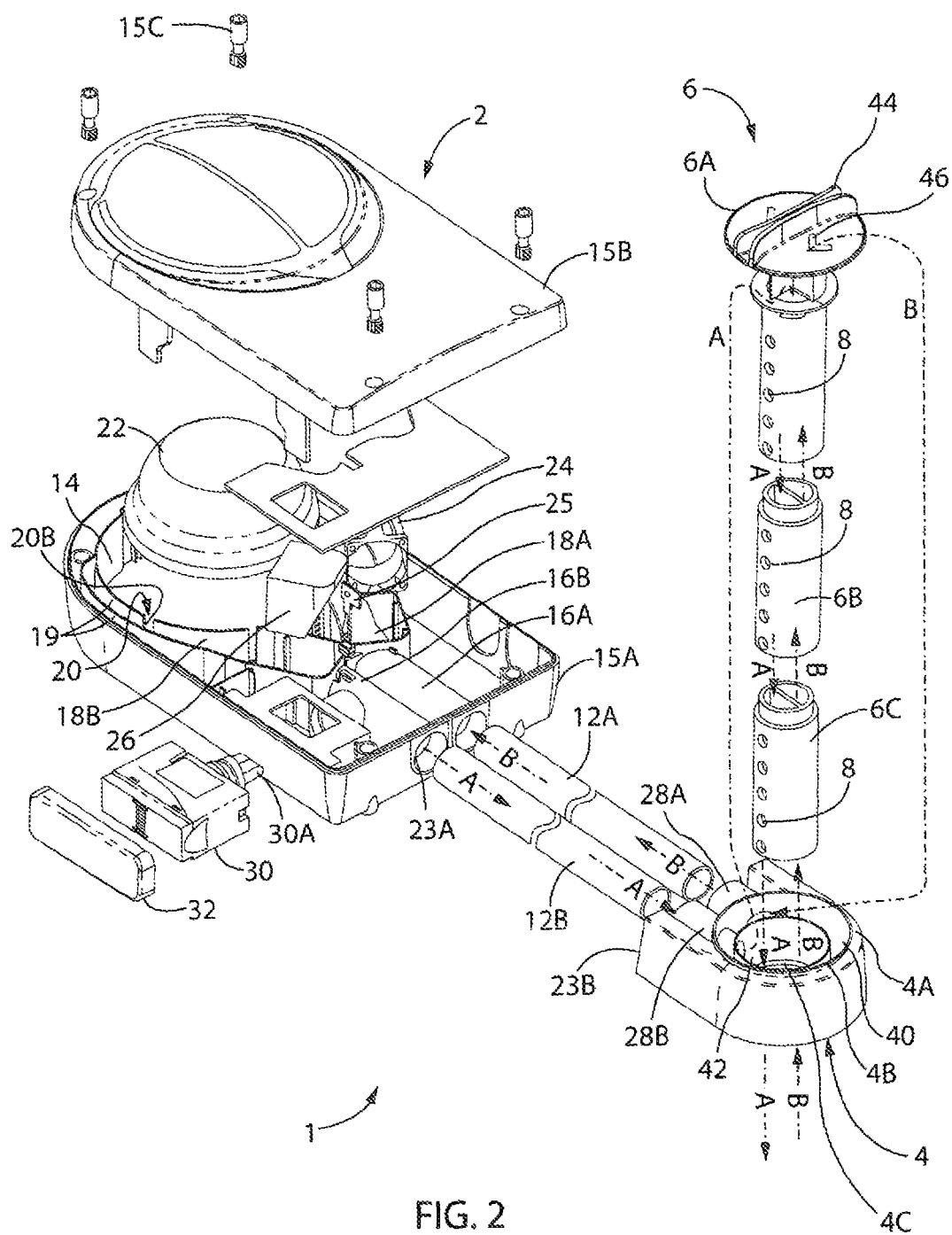
FIG. 2 is an exploded view of the duct detector of FIG. 1.

FIGS. 1 and 2 illustrate a duct detector 1 in accordance with a preferred embodiment of the invention. The duct detector 1 includes a detector unit 2 and a probe arrangement in the form of a probe unit 3 which is separable from the detector unit 2. A pair of conduits 12A and 12B connect the detector unit 2 and the probe unit 3 to allow the flow of fluid between them.

The detector unit 2 includes a detection region 14. A detection region is a region in which fluid is analysed. In this embodiment, the detection region has a detector module in the form of a point (or spot) detector mounted in it. Alternatively, by way of example, the detection region might be a detection chamber of an optical smoke detector or other volume.

The units 2, 3 are each mountable to the exterior of an HVAC duct. The probe unit 3 includes an elongate probe 6 which, in use, projects through an aperture in the wall of the duct into the interior of the duct. The probe 6 includes a series of ports in the form of simple apertures equally spaced along its length forming outlets 8 and another series of apertures forming inlets 10 (visible in FIG. 6). A stream of fluid representing a sample of the fluid in the duct travels into the probe 6 through the inlets 10, through a fluid circuit including the conduits 12A and 12B and the detector unit 2, and its detection region 14, before being returned to the duct via the outlets 8.

The probe unit 3 includes structure to separately connect the conduit 12A with the inlets 10 and the conduit 12B with the outlets 8. Thus conduit 12A delivers sample air to the detector unit 2 and the conduit 12B returns the sample air to the probe unit 3 where it is in turn returned to the duct via the outlets 8.

In this embodiment the detector unit 2 includes a housing 15 which is predominantly formed by an injection moulded base member 15A and a separate injection moulded lid 15B fastened thereto by self tapping mounting screws 15C. The lid is preferably transparent for ready inspection of inside the housing 15. The base member 15A is a tray like structure having a horizontal floor surrounded by upwardly projecting walls defining an internal region.

Tubular passages 16A and 16B are integrally formed with the housing 15 and open through one of the side walls to receive the conduits 12A and 12B respectively. The passages 16A, 16B each open into to a respective channel 18A, 18B. The channels 18A, 18B are defined by walls 19 which are integrally formed with and project upwardly from the floor of the base member 15A. The channels 18A, 18B open into the circular detection region 14 which, in this embodiment, is circular when viewed from above.

The lid 15B includes sealing structures complementary to the walls 19 to create a seal between the upper extent of the walls 19 and lid to thereby close the top of the channels 18A, 18B and detection region 14, to define conduits for conveying sample fluid to and from the detection region 14.

Figure 3:
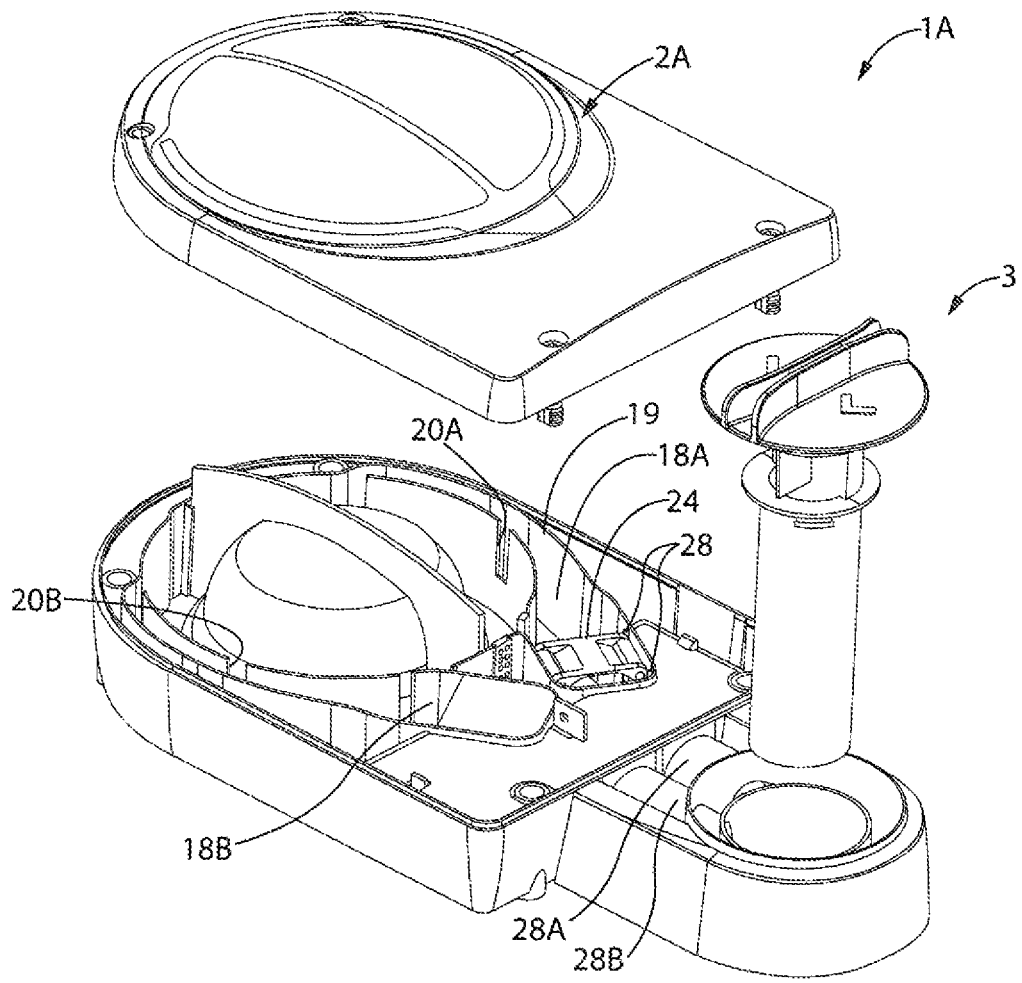
FIG. 3 is an exploded view of a duct detector in accordance with a further embodiment of the invention.
Figure 4:
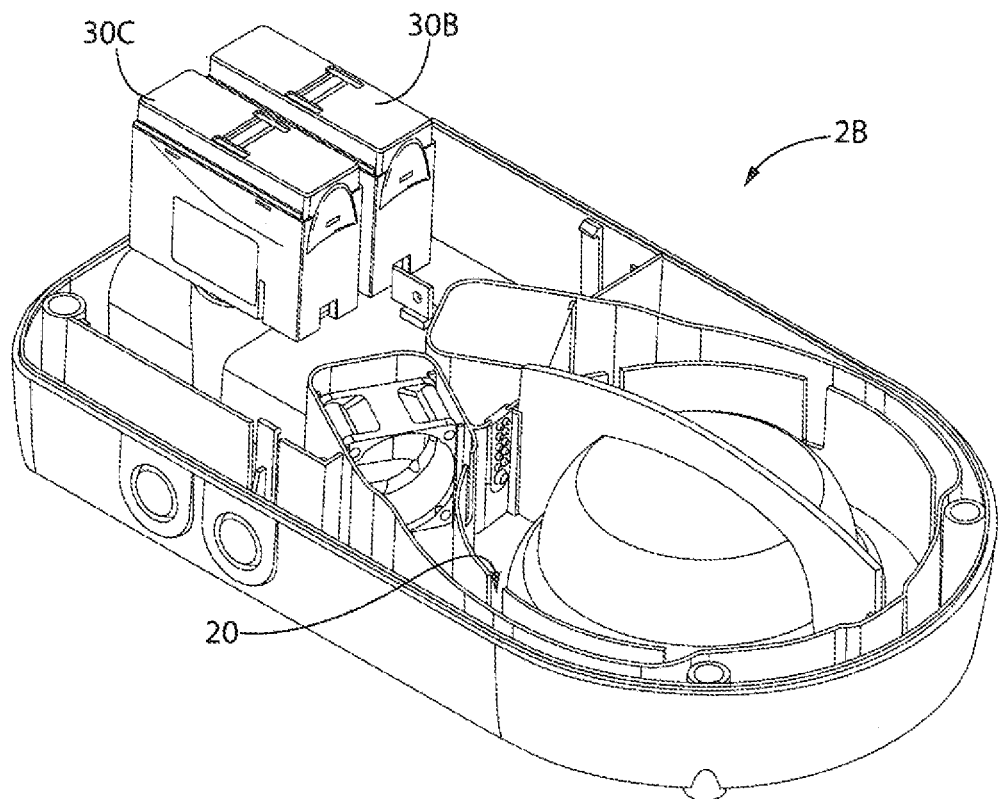
FIG. 4 is a perspective view of a detector unit in accordance with a further embodiment of the invention.

The innermost of the walls 19 separating the channels 18A, 18B and the detection region 14 each include a plurality of openings 20 to allow fluid to be communicated between the channels 18A, 18B and the detection region 14. Sample fluid received into the detector unit 2 via the inlet passage 16A is conveyed into the channel 18A then emerges from the openings 20A, as shown in FIG. 4 into the detection region 14. The sample air traverses the detection region 14 then passes through openings 20B into the channel 18B to be conveyed from the detector unit 2 via the passage 16B. Although openings 20A are not visible in FIG. 2, it should be understood that openings 20A is located across from openings 20B in substantially the same location as shown in FIG. 3.

In this embodiment the detection region 14 houses a detector module 22. A detector module is a device for providing a signal indicative of a characteristic of the sample fluid. In this embodiment the detector module 22 is an ionising type point detector for detecting smoke particles. The module 22 is circular when viewed in plan and is concentrically mounted within the circular detection region 14.

An aspect of the present invention provides a duct detector that is separable into a sender unit having a duct probe and a detector unit. The sender unit and detector unit can be closely coupled to each other, or physically separated from each other and kept in fluid communication by one or more air flow pipes. This is reflected in the embodiment of FIGS. 1 and 2 in the units 2, 3 being separable. Units 2, 3 are kept in fluid communication by pipes 12A and 12B when in a separate configuration as illustrated in FIGS. 1 and 2. FIG. 3 illustrates a duct detector 1A in which the detector unit 2A and the probe unit 3 are discrete separable units closely coupled to have the advantages of a discrete integral unit.

Figure 5:
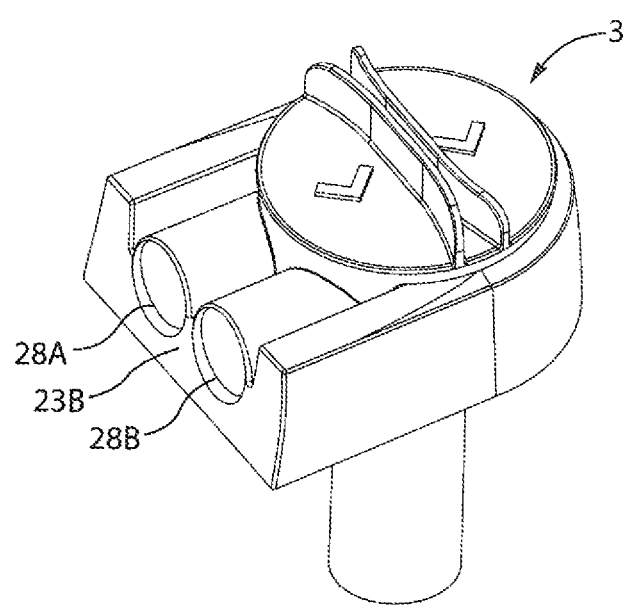
FIG. 5 is a perspective view of the probe arrangement of the duct detectors of FIGS. 1 to 3.

The probe unit 3 includes passages 28A and 28B which, form first and second fluid couplings that enable the probe unit, in the separated configuration of FIGS. 1 and 2, to connect with conduits 12A and 12B. In the close coupled configuration of FIG. 3 the passages 28A, 28B couple more directly with the passages 16A, 16B of the detector unit 2 (or 2A). To facilitate this cooperation it will be observed that in this preferred embodiment the passages 28A, 28B and 16A, 16B are mounted at a common, complementary, pitch and spacing from a planar surface when each of the units 2/2A, 3 are mounted to the planar surface. The latter requirement involves a complementary relationship between the distances between the passages of each unit and that unit's mounting features. The units 2, 3 can be directly connected to each other with fasteners, e.g. screws or the like. It may be necessary to use a short tube, inserted into passage 16A, 28A and 16B 28B to connect them together. Alternatively, the mounting faces 23A (on the detector unit 2) and 23B (on the probe arrangement 3), as shown in FIG. 5 can be fitted with a gasket to prevent leaks between the inlet and outlet.

Figure 8A:
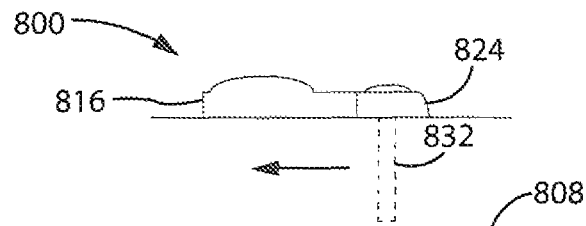
FIGS. 8A to 8D illustrate illustrative duct detector installations using embodiments of the present invention.

By separating the detector unit 2 and the probe unit 3 the difficulties of mounting the probe unit 3, and optimally locating the probe unit 3, are not so impacted by the physical bulk of the detector unit 2. As such the probe unit 3 can be mounted in an optimal position on a duct, which may be relatively confined and difficult to access. Whereas, the detector unit 2 can be mounted remotely therefrom at a more convenient location, e.g., on another part of the duct or on another support structure. In particular, the components requiring periodic checking and/or maintenance can be located within the detector unit 2 at the more convenient (e.g. accessible) location. FIGS. 8A to 9 illustrate several installation examples utilising this feature.

According to preferred forms of the invention the probe unit 3 is compact for ease of installation in confined spaces and the conduits 12A, 12B are flexible for easy routing. In preferred forms of the invention the compactness of the unit 3 is achieved at least partly through the absence of electronics and other complex components, which is in turn a consequence of moving all of the complex components (e.g. the detector module and the flow sensor etc.) to the detector unit 2.

In the close coupled configuration of FIG. 3 the fluid circuit between the probe unit's inlets and outlets is shorter, and therefore less restrictive, than the fluid circuit of the detector unit 1 in the separated configuration of figures FIGS. 1 and 2. In the close coupled configuration a satisfactory flow of sample air through the duct detector can be achieved without an aspirator. On the other hand, for operation in the separated configuration of FIGS. 1 and 2 it can be desirable to include an aspirator 24 to overcome the relatively higher resistance about the fluid circuit.

Of course separate aspirated and aspiratorless detector units could be provided, but preferably, and in accordance with another aspect of the invention, the detector unit is reconfigurable between aspirated and aspiratorless configurations. In the embodiments of FIGS. 1, 2 and 3 the channel portion 18A includes structure for receiving the aspirator 24. The structure is configured to maintain the integrity of the flow path to the detection region without the aspirator. In the embodiment of FIG. 3 this structure for receiving the aspirator 24 takes the form of spaced planar portions of the walls 19 of the channel 18A and opposed pairs of vertical ribs 28 spaced along the channel 18A and projecting a short distance from the opposed wall portions into the channel 18A. The aspirator 24 is received between the spaced portions of the walls 19 and axially located between and by the ribs 28.

Of course other implementations of this aspect of the invention are also contemplated. By way of example, rather than providing a flow path whose structure is maintained with or without the aspirator, the flow path could be partly defined by either one of an insertable aspiratorless module or an insertable module including an aspirator.

The aspirator module could include any type of device for causing airflow through the detector unit, for example, a pump, axial fan, centrifugal fan, tangential fan, etc.

In the embodiment of FIGS. 1 and 2, the detector unit 2 includes a second detector module in the form of a side mounted cartridge gas detector 30. This gas detector could be of any type, but preferably is VESDA ECO detector sold by Xtralis Pty Ltd, or a detector of the type described in the applicant's International patent application PCT/GB2010/050938 the contents of which are incorporated herein by reference.

The gas detector 30 has a broadly hexahedral exterior and is receivable within a complementary rectangular aperture in a side wall of the base member 15A. A probe 30A projects from the cartridge 30 and is receivable through an aperture in the side of the conduit 16B to draw and return a sub-sample of fluid to and from the conduit 16B. A blanking plate 32 is receivable within the rectangular aperture in the side wall of the base member 15A to close the aperture.

The gas detector 30, in this embodiment, is configured to detect pre-fire gasses (i.e. the gasses given off as a substance approaches ignition) to provide advance warning of a fire. It will be appreciated that the gas detector might be configured to detect other gasses, e.g. to detect refrigerant leaking from the HVAC system. The gas detector may be one for detecting the presence of at least one target species, such as $SO_2$, $NO_2$, $CL_2$, $CLO_2$, $CO_2$, $NH_3$, $HCl$, $HCN$, $NO$, $O_2$, $H_2$, $CO$, $H_2S$ or $CH_4$. Other volatile organic compounds (VOCs), as would be known in the art, may also be a target species. Different gas detectors are known to be responsive to different gases. Suitable detector types might be electrochemical sensors, catalytic diffusion sensors, explosimeters, infrared point sensors, non-dispersive infrared sensors, solid state metal oxide semiconductors, and/or photo ionization detectors.

The gas detector 30 defines its own internal detection region in which the pre-fire gasses are detected. As such, the detector unit 2 includes two detection regions. Of course other variants are possible. The detector unit 2A of FIG. 3 does not include a gas detector. The detector unit 2B of FIG. 4 includes a pair of top mounted gas detectors 30B and 30C.

A foam filter 26 is mounted within the channel 18B upstream of the gas detector 30 to protect the gas detector 30 from dust and debris. The channel 18B is defined by opposed planar wall portions and includes short ribs akin to wall portions and ribs 28 for mounting the aspirator 24 within the channel 18A.

A flow sensor 25 is mounted in the wall of the passage 16B between the filter 26 and the gas detector 30 to detect flow about the fluid circuit. In the absence of sufficient flow, a fault signal may be generated.

The probe unit 3 includes a probe 6 and a body 4. The probe 6 is made up of a spindle 6A and like extension pieces 6B and 6C. The body 4 pivotally carries the spindle 6A, and in turn the extension pieces 6B, 6C, and is mountable to the wall of a HVAC duct so that the probe 6 projects through an aperture in the wall of the duct and into the interior of the duct.

Figure 6:
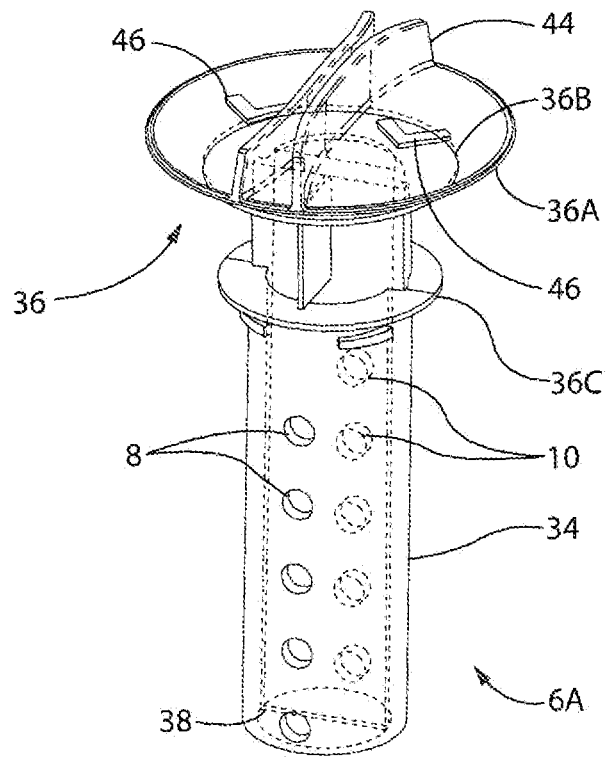
FIG. 6 is a perspective view of a spindle of a probe in accordance with an embodiment of the invention.

As best shown in FIG. 6, the spindle 6A includes a hollow projecting portion 34 for projecting into the duct and an upper portion 36 for cooperating with the body 4.

The hollow projecting portion 34 presents a cylindrical exterior and includes an internal planar divider 38 running along its length to divide its interior into a pair of half circular channels. The plurality of inlets 10 and outlets 8 each penetrate the cylindrical exterior of the portion 34 and open into a respective one of the half circular internal channels. As will be described each of these half circular channels is in fluid communication with a respective one of the passages 16A, 16B of the detector unit 2.

In another aspect, the present invention provides a duct probe having a modular construction to allow probes of different length to be created easily. An embodiment of this aspect of the invention is illustrated in FIGS. 1 and 2.

It will be appreciated that the body 4, spindle 6A, and a cap (not shown; for capping the open end of the portion 34) together constitute a functional probe unit. FIGS. 1 and 2 illustrate a probe unit 3 in which the probe 6 is extended by like extension pieces 6B and 6C. The extension piece 6B presents a stepped cylindrical exterior, the narrower portion of which is receivable within the open end of the spindle's projecting portion 34. As such the open end of the portion 34 constitutes structure to which the extension piece 6B is mountable. At its other end, spaced from its stepped cylindrical end, the extension piece 6B terminates in an open end like the open end of the portion 34 and is thereby adapted to cooperate with the stepped cylindrical end of the extension piece 6C. Accordingly the length of the probe 6 can be extended to suit ducts of different sizes.

It will be appreciated that this modular construction reduces the number of unique parts required in each installation, thus reducing inventory costs and production costs and improves the likelihood that a service or installation crew will have the appropriate parts at hand to suit any particular duct detector.

Figure 7:
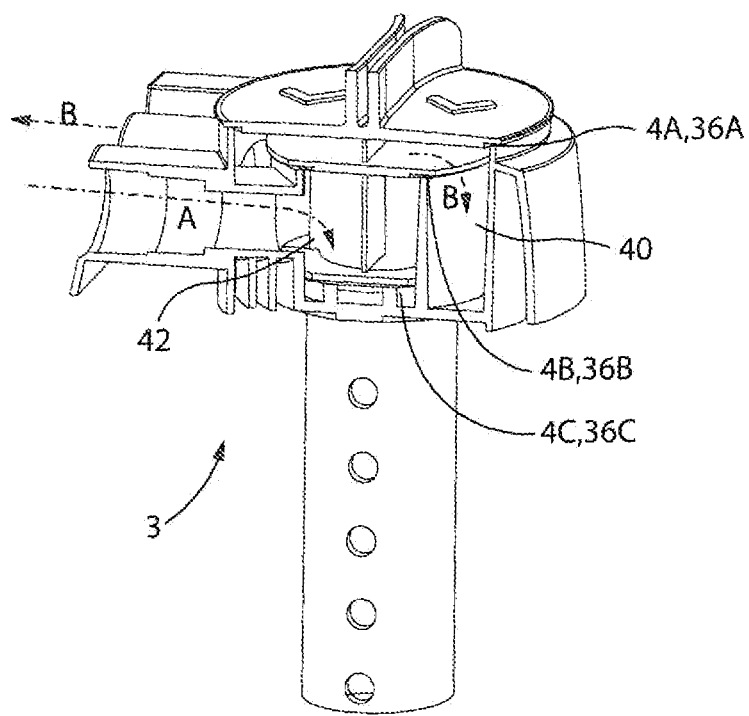
FIG. 7 is a cut away view of a probe arrangement in accordance with an embodiment of the invention.

In a broad concept, another aspect of the invention provides a duct detector having a fixed component that can be mounted in a fixed position relative to a duct and a reorientable duct probe mounted to the fixed component such that the duct probe can be reoriented with respect to the fixed component, to allow the duct probe to be reoriented with respect to the airflow in the duct. An embodiment of this aspect of the invention is best shown in FIGS. 2, 6 and 7.

The upper portion 36 of the spindle 6A includes three flanges 36A, 36B and 36C co-operable with circular sealing surfaces 4A, 4B and 4C of the body 4.

The flanges 36A, 36B, 36C project radially outwards and are axially spaced along the spindle 6A. The upper most flange 36A is of larger diameter than the downwardly adjacent flange 36B which is in turn of larger diameter than the lowest flange 36C. The sealing surfaces 4A, 4B, 4C are dimensioned and located to complement the flanges 36A, 36B, 36C whereby the upper portion 36 of spindle 6A cooperates with the body 4 to define manifold spaces 40, 42.

Each half circular flow path within the probe 6 opens in to a respective one of the two spaces defined between the three flanges 36A, 36B, 36C so as to open into a respective one of the manifold spaces 40, 42.

The body 4 is an integrally formed structure and defines the passages 28A, 28B. It will be appreciated from FIGS. 2 and 7 the body provides two manifold spaces 40, 42. The manifold space 40 is generally annular and encircles the manifold space 42. Passage 28A opens into the manifold space 40. Passage 28B extends across the manifold space 40 and opens into the manifold space 42. As indicated by arrows A and B, air travels through the inlet of the probe 6 that extends up through manifold 42 and into annular manifold 40, then into the detector via pipe 28A. Air exits the detector via pipe 28B which exhausts into manifold 42. The arrow marked B indicates the incoming flow, before detection, and the arrow marked A indicates the exhaust flow after analysis. Similar arrows are also indicated FIG. 2.

A handle 44 is integrally formed with, and carried atop, the flange 36A of the spindle 6A. The handle 44 can be manipulated by hand so that the probe 6 may be rotated about its axis within the body 4. By manipulating the handle 44 a user may orient the probe relative to the airflow within the duct and the body 4. This allows the probe unit 3 to be mounted to the duct without careful alignment, and the probe aligned later so as to facilitate easier installation in difficult working environments, without compromising the rotational orientation of the probe.

Indicia, e.g., arrows 46, are also carried atop and integrally formed with the flange 36A. Arrows 46 constitute an indicator indicating the relative orientation of the inlets 8 and outlets 10. In this embodiment the inlets 8 and outlets 10 open in opposite directions. By aligning the arrows 46 to the direction of flow in the duct, an installer can be confident that the inlets 8 face directly upstream and the outlets 10 face directly downstream whereby pressure differences between these two positions drive fluid through the duct detector 1.

As will be appreciated the form of the probe used in this aspect of the invention can be varied. For example the probe can include multiple probes, e.g. a dedicated inlet and dedicated outlet probe that are either mounted to a common re-alignable base.

As noted above a flow sensor can be mounted the flow path through the detector portion of the duct detector, to detect flow about the fluid circuit. The flow sensor can be a thermal flow sensor; ultrasonic flow sensor, or other type of flow sensor.

During installation a technician can check if the pressure drop across the probe is causes an acceptable flow rate through the detector using a flow sensor, such as the onboard flow sensor, and in the event that the flow rate is below a predetermined level an aspirator module can be fitted to the system in a manner described above.

A preferred form of the invention incorporates a device, e.g. a turbine, for extracting power from the flow in the duct to generate electricity to power at least part of the duct detector. The extraction device could be mounted within the duct detector downstream of the duct detector's sampling inlet, but preferably is directly exposed to the flow in the duct. For example, the extraction device might take the form a simple windmill-like turbine carried by the probe.

The system can additionally include energy storage system configured to store power for supply to another device.

The duct detector preferably includes an energy storage device to power at least part of the duct detector or the at least part of the duct detector or an external device. The storage device is preferably charged by the extraction device. The storage device may be or include one or more of a battery, and capacitor and a supercapacitor or the like.

To facilitate connection to external devices the duct detector of can further include an electrical connector adapted to enable an electrical connection of the energy storage device to the other device or an electrical transmission system to which the device is connected.

FIGS. 8A to 8D are schematic depictions of several illustrative duct detector installations using embodiments of the present invention. Each of the installations includes a duct detector system 800 to 806 mounted to a respective section of duct 808 to 814. The duct detector systems 800 to 806 include a detector unit 816 to 822 and a probe unit 824 to 830. The probe unit 824 to 830 is mounted to the duct 808 to 814 in each case such that its probe 832 to 836 is positioned in an airflow in the duct 808 to 814. It will be appreciated that the probe of the duct detector system 804 cannot be seen in the figure due to the orientation of the probe unit on the duct 812. The four illustrated installations differ from each other in the relative mounting of their detector unit 816 to 822 and probe unit 824 to 830.

Turning firstly to FIG. 8A, the detector unit 816 and probe unit 824 are mounted in a close coupled configuration. In an installation of this type, the duct detector 800 approximates a conventional duct detector having a unitary housing that contains the detection chamber and probe within it. The duct detector 800 is mounted such that the detector unit 816 and probe unit 824 are substantially or actually in contact with each other. Most preferably the detector unit 816 and probe unit 824 are rigidly mechanically connected to each other.

Figure 8B:
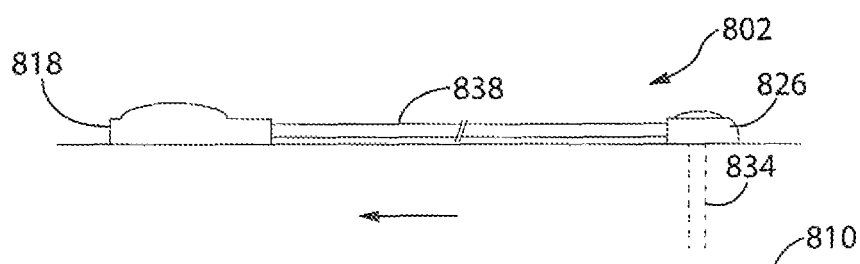
Figure 8C:
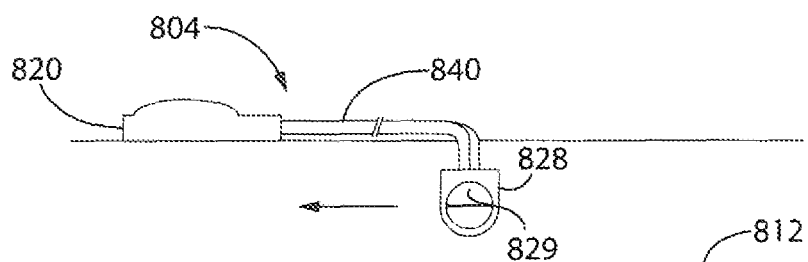
Figure 8D:
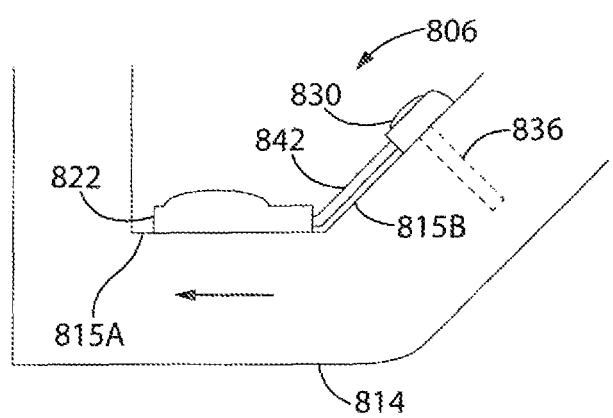
Figure 9:
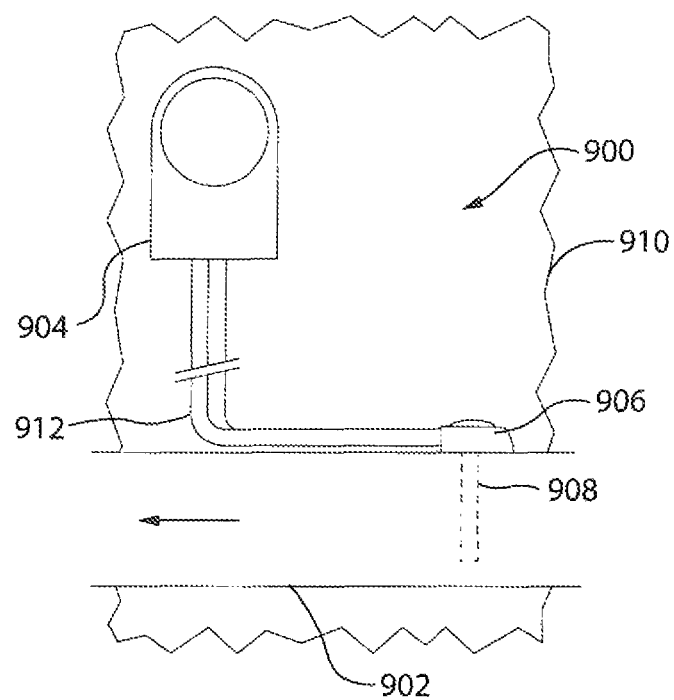
FIG. 9 illustrates another duct detector installation using an embodiment of the present invention.

In FIGS. 8B to 8D the detector unit 818 to 822 and their respective probe unit 826 to 830 are mounted in the separated configuration.

In FIG. 8B the duct detector system 802 includes a detector unit 818 and probe unit 826 that are mounted remotely from each other on a common side of the duct 810. The probe unit 826 is mounted to the duct 810 in each case such that its probe 834 is positioned in an airflow in the duct 810. The units are connected by a pair of straight elongate conduits 838.

In FIG. 8C the detector unit 820 and probe unit 828 are mounted remotely from each other on different sides of the duct 812. In this case the elongate conduit 840 that connects them includes at least one and possibly more bends. The conduit 840 can be made from a flexible conduit; lengths of straight stiff conduit connected with curved sections or a combination of flexible and stiff conduit. As can be seen, the top of probe unit 828 includes indicia 829 which indicates the direction of alignment of the inlet and outlet ports on the probe (not shown), so that the installed can determine that the probe is aligned with the direction of flow (indicated by an arrow in the figures). FIG. 8D illustrates a case where the detector arrangement 806 is fitted to a duct 814 with a complex shape, which includes a sharp coiner and a curve. As can be seen the duct section 815A, between the corner and curve, is too short for the detector 806 to be mounted in close coupled configuration. Therefore, in this case the detector unit 822 and probe unit 830 are mounted remotely from each other on sections 815A and 815B of the duct 814 respectively that are extended in different directions. The elongate conduit 842 that connects them includes a bend to accommodate the different alignment of the surfaces on which the detector unit 822 and probe unit 830 are mounted.

FIG. 9 illustrates a further example of a duct detector system. In this example the duct detector system 900 includes a detector unit 904 and a probe unit 906. The probe unit 906 is mounted to the duct 902 as described in the previous examples with a probe 908 positioned in an airflow in the duct 902, but the detector unit 904 is mounted remotely on a wall 910. The detector unit 904 and probe unit 906 are connected by a conduit 912. As noted above the conduit can be rigid or flexible, or a combination thereof.

If convenient the detector unit and probe unit can be mounted together in the close coupled configuration, similar to the installation of a conventional duct detector, or if needed the detector unit and probe unit can be separated and mounted remotely from each other. This can enable the detector unit to be mounted in a convenient location e.g. for inspection and electrical connection and the probe unit can be mounted in a convenient or preferred position for detection performance. Conveniently, in the separated configuration the orientation and positioning of either or the units does not directly affect the orientation and positioning of its corresponding other unit, as differences in positional and orientation can be accommodated in the conduit layout.

In these examples the detector unit is preferably connected to a fire alarm system, HVAC control system, or other control system. The connection can use a wired or wireless communications channel. The communications channel can be used to communicate particle detection or system fault events to the fire alarm system, HVAC control system, or other control system.

It will be appreciated from the foregoing that the various aspects of the detector described herein can be used singly in duct detectors or combined into a unit having all of the aspects of the invention.

It is believed that the modularity provided by the preferred embodiments described herein can greatly increase flexibility of the duct detector and decrease the inventory requirements for installers. For instance a single duct detector can be installed in its most basic close-coupled, aspiratorless configuration if that suits the circumstances. The same duct detector can also be used in a more complex installation by mounting the detector unit remotely from the probe unit connected by conduits. By the addition of a plug-in aspirator module, a suitable flow rate to be achieved. This reduces the range of inventory carried by an installer and improves the likelihood that a service or installation crew will have the appropriate parts at hand to suit a new installation.

The general particle and gas detection functionality have not been described herein in detail as these will be readily known to those skilled in the art. For example the particle detection, alarm monitoring and notification, fault monitoring, flow detection and other standard functionality of particle detectors can be implemented in a similar way to the particle detection devices sold under the brand name ICAM by Xtralis Pty Ltd.

It will be understood that the invention disclosed and defined in this specification extends to all alternative combinations of two or more of the individual features mentioned or evident from the text or drawings. All of these different combinations constitute various alternative aspects of the invention.

The claims defining the invention are as follows:

1. A port unit for a duct detector, the port unit including a portion mountable to a duct independently of the duct detector and having one or more ports configured to open into the interior of the duct in use; the port unit being separable from a portion of the duct detector including a detection region, and being attachable to the portion of the duct detector including the detection region via one or more conduits to provide fluid communication between them.

2. The port unit of claim 1 being a probe arrangement including at least one probe having the one or more ports and extending from the mountable portion to extend into the interior of the duct to position the port(s) in the duct.

3. The port unit of claim 2 wherein the probe includes:
   a portion having one or more ports and extending from the mountable portion to extend into the interior of the duct to position the port(s) in the duct; and structure to which an extension piece having one or more ports is mountable.

4. The port unit of claim 1 wherein the unit includes mating structure configured to engage the portion of the duct detector including the detection region, to enable engagement of the port unit and portion of the duct detector including the detection region in a mated configuration.

5. The port unit of claim 1 wherein the unit includes mating structure configured to engage the one or more conduits to enable connection of the port unit to the portion of the duct detector including the detection region when separated and mounted separate from each other.

6. A port unit for a duct detector, the port unit including:
   a portion mountable to a duct independently of a particle detector;
   a single probe for insertion into the duct in use and projecting from the mountable portion, the probe including a first passage having at least one inlet port for receiving a sample of flow from the duct; and a second passage having at least one outlet port for returning the sample to the duct; and
   a first fluid coupling being adapted for connection to an inlet of the particle detector and being in fluid communication with the first passage; and
   a second fluid coupling being adapted for connection to an outlet of a particle detector and being in fluid communication with the second passage.

7. The port unit as claimed in claim 6 wherein the probe is rotatable relative to the portion mountable to the duct to enable the probe to be re-oriented with respect to the portion mountable to the duct, such that the at least one inlet and outlet are aligned with a direction of flow in the duct.

8. A duct detector including: a port unit including one or more ports, said port unit being mountable to a duct in use so as to position the one or more ports in the duct; and a detector unit including a detection region; the port unit and detector unit being reconfigurable between a mated configuration and a separated configuration in which the port unit and detector unit are mountable to the duct with a variable separation between them and coupled by one or more conduits to provide fluid communication therebetween.

9. The duct detector of claim 8 wherein the ports include:
   one or more inlets for receiving a sample of flow from the duct;
   one or more outlets for returning the sample to the duct; and wherein
   the detection region is between the inlets and the outlets;

the one or more inlets and the one or more outlets being configured such that in use, flow in the duct to which the port unit is mounted drives a sample flow through the detector unit for aspiratorless operation in the mated configuration.

10. The duct detector of claim 8 which further includes structure for receiving an aspirator configured to drive a sample flow through the detector unit for aspirated operation in the separated configuration.

11. The duct detector of claim 8 wherein in the mated configuration the port unit and detector unit are, rigidly mated to each other.

* * * * *